United States Patent [19]
Carlson et al.

[11] Patent Number: 5,464,360
[45] Date of Patent: Nov. 7, 1995

[54] CONTAINER FOR SHIPPING AND UTILIZING STINGING INSECTS

[76] Inventors: Robert R. Carlson; Stephanie Carlson, both of 8 Sheffield Ave., W. Babylon, N.Y. 11704

[21] Appl. No.: 272,570

[22] Filed: Jul. 11, 1994

[51] Int. Cl.⁶ .................................................. A01K 49/00
[52] U.S. Cl. .................................................. 449/27; 449/3
[58] Field of Search ............................. 449/3, 7, 8, 9, 449/11, 27, 28; 119/6.5

[56] References Cited

U.S. PATENT DOCUMENTS

| 2,249,401 | 7/1941 | Sieg | 401/176 |
| 5,135,429 | 8/1992 | Gefen et al. | 449/28 X |

FOREIGN PATENT DOCUMENTS

| 242919 | 1/1912 | Germany | 449/27 |
| 121620 | 1/1959 | U.S.S.R. | 449/28 |

*Primary Examiner*—Robert P. Swiatek
*Attorney, Agent, or Firm*—Norman B. Rainer

[57] ABSTRACT

A container for shipping and utilizing stinging insects for therapeutic purposes includes an elongated sidewall portion having uniform cross-sectional configuration along a center axis of elongation, and end closures disposed at front and rear extremities of the sidewall. One of the end closures is a mesh panel which prevents passage of insects but permits stinging therethrough. A wafer, slideably positionable within the container permits isolation of one insect and advancement of the insect to the mesh panel which may be held against the patient's skin.

10 Claims, 2 Drawing Sheets

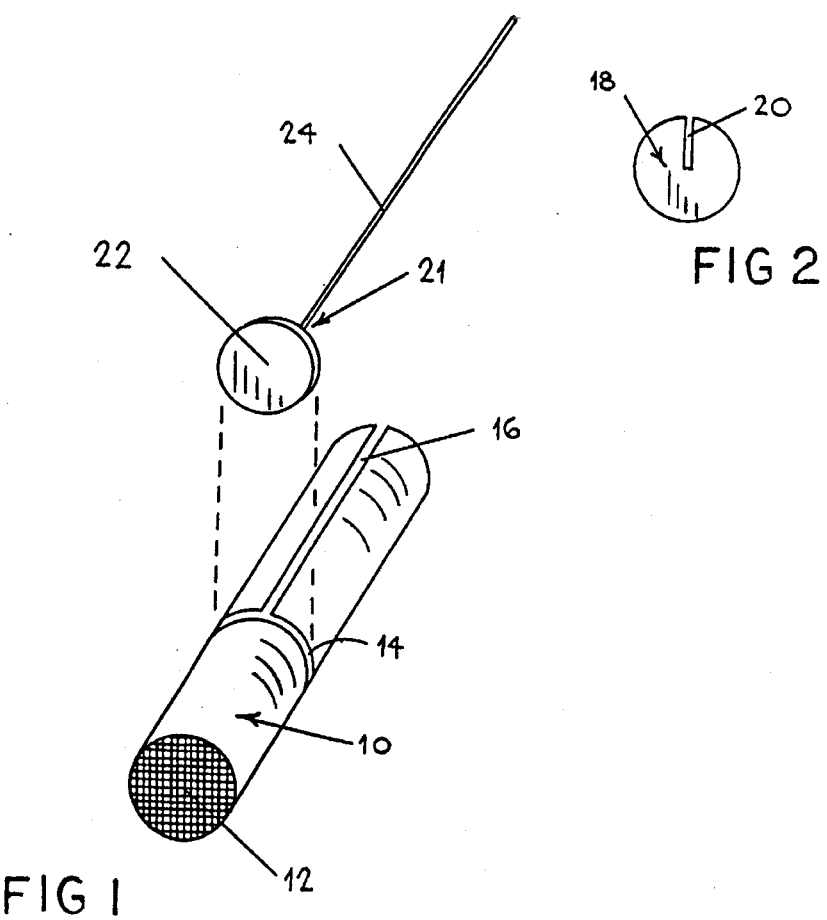
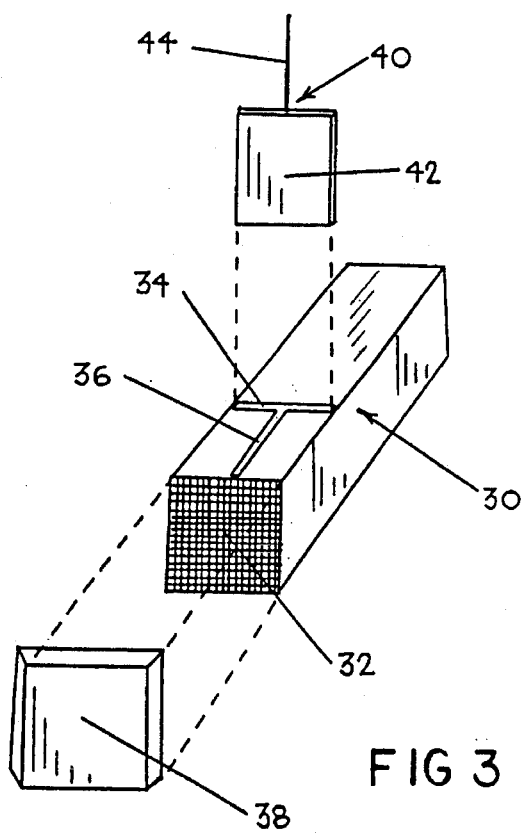

CONTAINER FOR SHIPPING AND UTILIZING STINGING INSECTS

DISCLOSURE DOCUMENT

The invention described herein is the subject of Disclosure Document 338626, recorded Aug. 23, 1993, and Disclosure Document 345414, recorded Jan. 03, 1994.

BACKGROUND OF THE INVENTION

1. Field of the Invention

This invention concerns the use of stinging insects for therapeutic purposes, and more particularly relates to a container for shipping live bees and further serving as a sting applicator.

2. Description of the Prior Art

The controlled application of bee stings to human skin has been found beneficial in the treatment of multiple sclerosis and arthritis.

Containers for the shipment of live bees, as by way of the mail service, are disclosed in U.S. Pat. No. 4,718,134 and 4,524,476. Said containers generally provide for an adequate supply of air and food to sustain provision for the special use of the bees in sting therapy. U.S. Pat. No. 4,158,267 concerns a container for use by fishermen for carrying live insects and dispensing said insects one at a time.

Because persons requiring sting therapy generally do not have proper expertise and equipment for handling live bees, it is highly desirable that the bees be made available in a substantially dosage-controlled, safe and easily utilized format. Since live bees are not as readily available as ordinary medicinal agents, it is necessary that the bees be shipped directly from the supplier to the user.

It is accordingly an object of this invention to provide a shipping container for live insects that also serves as a controlled dosage application of stings.

It is another object of the present invention to provide a container as in the foregoing object which is of simple construction amenable to low cost manufacture.

These and other beneficial objects and advantages will be apparent from the following description.

SUMMARY OF THE INVENTION

The above and other beneficial objects and advantages are accomplished in accordance with the present invention by a container comprised of an elongated sidewall portion having substantially uniform cross-sectional configuration along a center axis of elongation, end closures disposed at both extremities of said sidewall portion, divider means disposed within said container transversely to said axis for establishing axially adjacent residence and sting-applying chambers, means for effecting selection of insects within said container, and means for advancing said selected insects into said sting-applying chamber.

In a preferred embodiment, said sting-applying chamber is defined in part by a mesh panel which prevents passage of said insects but permits the insect to achieve stinging through said panel. In such embodiment, a removable solid panel covers said mesh panel to prevent inadvertent Stinging during shipment of the container. Containers of this invention, empty of bees, could be held in inventory by medical clinics which practice bee sting therapy. Local beekeepers could load the containers, as needed, for the medical clinics.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 1 is an exploded perspective view of a first embodiment of the container of the present invention.

FIG. 2 is a rear view of the embodiment of FIG. 1.

FIG. 3 is an exploded perspective view of a second embodiment of the container of this invention.

DESCRIPTION OF THE PREFERRED EMBODIMENT

Figure 4:
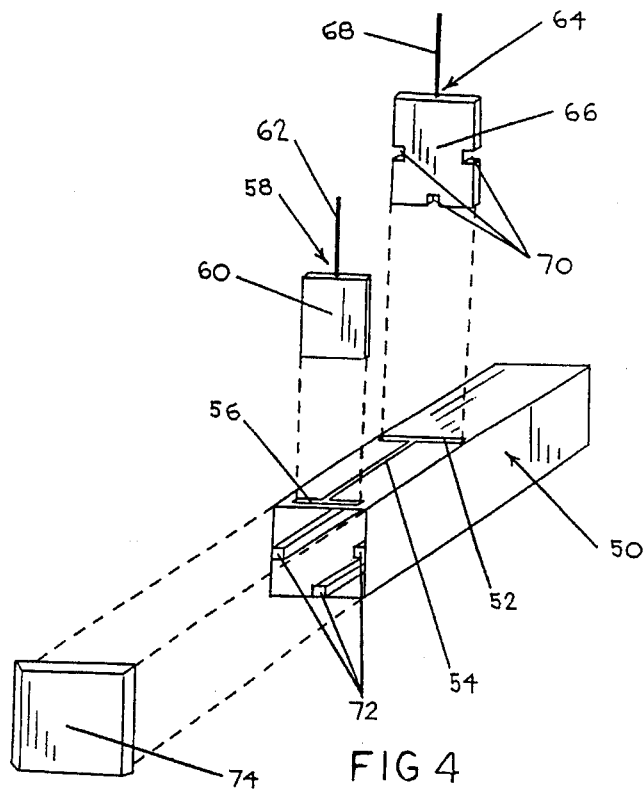
FIG. 4 is an exploded perspective view of a third embodiment of the container of this invention.

FIGS. 1 and 2 illustrate an embodiment of the container of this invention constructed as a cylindrical tube 10. The tube 10 has a screen 12 on the front end. A lateral insertion slot 14 is disposed on the upper half of tube 10, having the shape of a half circle. A longitudinal insertion slot 16 on top runs along the rear portion of tube 10. FIG. 2 shows the rear plug 18 which is positioned at the end opposite screen 12. The rear plug 18 is made with a rear insertion slot 20. The rear insertion slot 20 unites with longitudinal insertion slot 16. The three insertion slots allow entry of the insect pusher 21 into the tube 10. The insect pusher 21 consists of a circular wafer 22 and a push rod 24. The push rod 24 can be made to screw into the center of the circular wafer 22 or the two can be constructed as a single unit. The push rod 24 is slightly longer than the length of tube 10. The forward portion of tube 10, bounded by screen 12 and slot 14, is a sting-applying chamber. The rearward portion of tube 10, bounded by slot 14 and rear plug 20, is a residence chamber.

The container device of this invention is adapted to confine a desired number of insects. To use the device:

1. The insects are all shaken down into the residence chamber.

2. The insect pusher 21 is then introduced into the cylindrical tube 10 through the three insertion slots. The insects are now all held in the residence chamber by circular wafer 22.
   Note: If the container device had only one insect left, or were supplied with only one insect, then the insect could just be shaken into the sting-applying chamber by itself before introducing the push rod 21 into tube 10. Then skip the next step.

3. To allow insect(s) into the sting-applying chamber, the end of the push rod 24, which protrudes through the end of the rear plug 18, is lifted little by little. This gradually raises circular wafer 22 up out of slot 14 until insect(s) begin moving under wafer 22 from the residence chamber into the sting-applying chamber. When the desired number of insect(s) (presumably one) have moved into the sting-applying chamber, pusher 21 is lowered back down to the bottom of tube 10.

4. With the desired number of insects in the sting-applying chamber, the screened front end of the device is placed against the user's skin.

5. The insect pusher 21 is used to push the insect(s) in the sting-applying chamber up against the screen.

6. The insect will sting the user through the screen as it is pushed into the screen.

FIG. 3 illustrates a second variation of the container device, constructed as a rectangular box 30. The box 30 has a screen 32 on the front end. A lateral insertion slot 34 is located on top of the box. A longitudinal slot 36 runs along the middle of the top of the box 30. The longitudinal slot runs from lateral insertion slot 34 to the screen 32. The lateral insertion slot 34 allows entry of insect pusher 40 into the box 30. The insect pusher 40 consists of a paddle 42 and a stem 44. The stem 44 is used to move the insect pusher 40 towards screen 32. The longitudinal slot 36 allows the stem 44 to project up out of the top of the box 30 as the insect pusher 40 is moved forwardly. The forward portion of box 30 located between screen 32 and lateral insertion slot 34 is the sting-applying chamber. The portion of box 30 located behind slot 34 is the residence chamber. The embodiment of FIG. 3 has a removable cap 38 which is used to prevent inadvertent stinging through screen 32.

This variation of the container device is used in a manner similar to the use of the first embodiment exemplified in FIGS. 1 and 2:

1. The insects are all shaken down into the residence chamber.

2. The insect pusher 40 is then introduced into the rectangular box 30 through lateral insertion slot 34. The insects are now all held in the residence chamber by paddle 42.

3. To allow insect(s) into the stringing-applying chamber, stem 44 is lifted gradually. This slowly raises paddle 42 up out of lateral insertion slot 34 until insect(s) begin moving under the paddle from the reidence chamber into the sting-applying chamber. When the desired number of insect(s) (presumably one) have moved into the sting-applying chamber, pusher 40 is lowered back down to the bottom of box 30.

4. With the desired number of insects in the sting-applying chamber, the screened front end of the sting applicator is placed against the user's skin.

5. The insect pusher 40 is held by stem 44, which protrudes up through the longitudinal slot 36, and pushed up against the screen 32.

6. The insect will sting the user through the screen 32 as it is pushed into the screen The third embodiment of the container device, as illustrated in FIG. 4, does not employ a screen at the front end. As in FIG. 3, the device consists of a cylindrical box 50, a lateral insertion slot 52, a longitudinal slot 54, a removable cap 74, and an insect pusher 64. The insect pusher 64 is constructed essentially as in FIG. 3, with a paddle 66 and a stem However, paddle 66 is made with stability notches 70 on the bottom and sides. The notches fit over stability rails 72 on the bottom and sides of box 50. The notches 70 and rails 72 interact to prevent the paddle 66 from wobbling as pusher 64 is moved forward. Rather than a screen, this variation employs an insect releaser 58 which is constructed with a paddle 60 and stem 62, similar to the insect pusher 64. The insect releaser 58 fits into the forward insertion slot 56.

The third embodiment is used in much the same way as the second embodiment. The insects are shaken down into the residence chamber, and insect pusher 64 is then inserted into the lateral insertion slot 52. The cap 74 is removed and the insect releaser 58 is inserted into the forward insertion slot 56. The insect pusher 64 is raised until the desired number of insects have moved under paddle 66 into the stinging-applying chamber. The front end of the device is placed up against the skin and the insect releaser 58 is pulled out of forward insertion slot 56. The insect pusher 64 is moved forwardly, pushing the insect(s) up against the skin.

Figure 5:
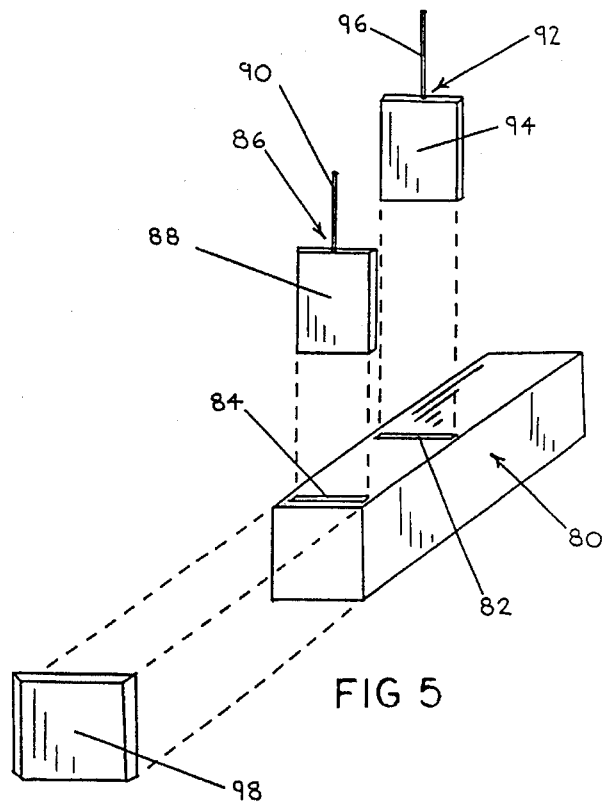
FIG. 5 is an exploded perspective view of a fourth embodiment of the container of the present invention.

FIG. 5 examplifes a further embodiment of the container device of this invention, and is not equipped with a longitudinal slot. The cylindrical box 80 has a lateral insertion slot 82, a forward insertion slot 84, a removable cap 98, and an insect releaser 86 comprised of a paddle 88 and stem 90. This embodiment also has a divider 92 with a paddle 94 and stem 96. Since this version has no longitudinal slot, the insect(s) cannot be induced to sting by pushing the divider 92 forwardly. To use this embodiment of the device, insect releaser 86 is inserted into forward insertion slot 84, the desired number of insects are allowed into the sting-applying chamber, and cap 98 is removed. The device is then shaken vigorously, annoying the insects inside. The front end is placed against the skin, and when the insect releaser 86 is pulled out, the annoyed insect will react.

Figure 6:
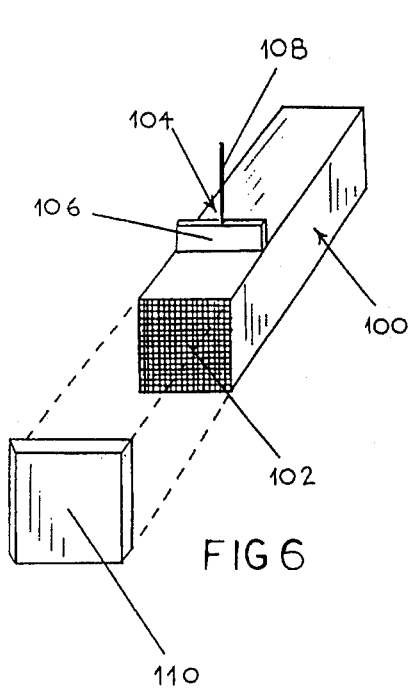
FIG. 6 is a partially exploded perspective view of a fifth embodiment of the container of the present invention.

The fifth embodiment of the container device, illustrated in FIG. 6, is similar to the fourth embodiment, but uses a screen 102 at the front end rather than an insect releaser. The cylindrical box 100 is equipped with a removable cap 110 and divider 104. The divider 104 is constructed as before with a paddle 106 and stem 108. The lateral insertion slot which the divider 104 fits into is not visible in this view, as the divider 104 is shown partially inserted into the box 100. In use, once the desired number of insects are in the sting-applying chamber, the applicator is vigorously shaken. The annoyed insect(s) will then sting through the screen 102. If only one insect were supplied with the sting applicator of FIG. 6, then the divider 104 would not be required.

Although five embodiments of the container device have been described, there are innumerable variations. The device has been shown as a cylindrical tube and a rectangular box, but other shapes of cylindric or prismatic contour are possible. The applicator may be fabricated of various materials such as wood, plastic such as PLEXIGLAS or metal. The screen could also be constructed from a variety of materials (e.g., metal or plastic fiber). The mesh size is such as to be small enough to prevent passage of the insects, but large enough for the insect's stinger to fit comfortably through. The insects are allowed into the sting-applying chamber by raising the insect pusher/divider in the adaptions described, but other methods could be used. For example, the paddles could be constructed with an aperture in the middle that would be opened or closed by turning the paddle stem. The size of the container device is not critical, so long as it comfortably holds the desired number of bees. The dimensions of the insect pusher/insect releaser/divider and insertion slots are also not critical, although the insertion slots must obviously be made narrow enough to prevent escape of the insects.

The procedures suggested for using the device are merely exemplary. There are other ways in which the device could be used. For example, some users might prefer to repeatedly push the insect sharply with the insect pusher until it stings, rather than pushing it flat up against the screen or skin. Or to take another example, some strains of honey bees are so aggressive that they would not need to be shaken or pushed at all to induce stinging (The africanized—or so called "killer"—honey bees being the most notorious in this respect).

Those experienced in the field will recognize that the described container device can readily be adapted to double as insect mailing boxes. Food and ventilation could be provided, as is now done with bee mailing boxes, for example. The insect pusher/insect releaser/divider could be associated with the inside or outside of the device in a variety of ways for mailing.

It will also be clear that the variations illustrated in FIGS. 4 and 5 could be used as insect distribution units.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described our invention, what is claimed is:

1. A container for transporting live insects and facilitating controlled therapeutic application of stings by said insects to the skin of a patient, said container comprised of an elongated sidewall portion having substantially uniform cross-sectional configuration along a center axis of elongation, end closures disposed at front and rear extremities of said sidewall portion, divider means disposable within said container transversely to said axis for establishing axially adjacent residence and sting-applying chambers and for effecting selection of insects and advancement of said selected insects into said sting-applying chamber.

2. The container of claim 1 wherein one end closure is a mesh panel disposed transversely to said axis, said panel preventing passage of insects but permitting stinging therethrough.

3. The container of claim 2 having a solid panel that removably covers said mesh panel.

4. The container of claim 3 wherein said sidewall portion has a first lateral slot disposed transversely to said axis.

5. The container of claim 4 wherein said sidewall portion has a longitudinal slot disposed in parallel relation to said axis and communicating with said first lateral slot.

6. The container of claim 4 wherein said divider means is comprised of a wafer attached to a manipulation rod, said wafer having a thickness permitting close-fitting insertion through said first lateral slot and having a perimeter matching the cross-sectional configuration of said chambers to permit close-fitting sliding axial movement.

7. The container of claim 1 wherein said sidewall portion has a first lateral slot disposed transversely to said axis, and an auxiliary lateral slot disposed in parallel spaced apart relationship to said first lateral slot.

8. The container of claim 7 wherein said divider means is comprised of two wafers, each attached to a separate manipulation rod, said wafers each having a thickness permitting close-fitting insertion through said first and auxiliary lateral slots and having perimeters matching the cross-sectional configuration of said sidewall portion.

9. The container of claim 1 wherein said sidewall is of rectangular prismatic contour.

10. The container of claim 1 wherein said sidewall is of circular cylindrical contour.

* * * * *